(12) United States Patent
Maass et al.

(10) Patent No.: US 10,304,671 B2
(45) Date of Patent: May 28, 2019

(54) METHOD FOR COMPUTER-ASSISTED ANALYSIS OF ONE OR MORE TISSUE SECTIONS OF THE HUMAN OR ANIMAL BODY

(71) Applicant: BRUKER DALTONIK GMBH, Bremen (DE)

(72) Inventors: Peter Maass, Bremen (DE); Dennis Trede, Bremen (DE); Fedor Aleksandrov, Bremen (DE); Janina Oetjen, Lilienthal (DE); Lena Hauberg-Lotte, Bremen (DE)

(73) Assignee: BRUKER DALTONIK GMBH, Bremen (DE)

( * ) Notice: Subject to any disclaimer, the term of this patent is extended or adjusted under 35 U.S.C. 154(b) by 260 days.

(21) Appl. No.: 14/959,967

(22) Filed: Dec. 4, 2015

(65) Prior Publication Data
US 2016/0163523 A1 Jun. 9, 2016

(30) Foreign Application Priority Data
Dec. 4, 2014 (DE) .................. 10 2014 224 916

(51) Int. Cl.
| | | |
|---|---|---|
| *G01N 33/48* | (2006.01) | |
| *H01J 49/00* | (2006.01) | |
| *G16B 40/00* | (2019.01) | |
| *H01J 49/16* | (2006.01) | |
| *G06G 7/58* | (2006.01) | |
| *G01N 1/31* | (2006.01) | |

(52) U.S. Cl.
CPC .......... *H01J 49/0036* (2013.01); *G16B 40/00* (2019.02); *H01J 49/0004* (2013.01); *H01J 49/164* (2013.01); *G01N 1/312* (2013.01)

(58) Field of Classification Search
None
See application file for complete search history.

(56) References Cited

U.S. PATENT DOCUMENTS

| | | |
|---|---|---|
| 2009/0154781 A1 | 6/2009 | Bogdan |
| 2012/0269417 A1 | 10/2012 | Bautista et al. |
| 2013/0060550 A1 | 3/2013 | Dumas et al. |

FOREIGN PATENT DOCUMENTS

| | | |
|---|---|---|
| DE | 10 2013 207 402 A1 | 10/2014 |
| WO | WO 02/10740 A2 | 2/2002 |
| WO | WO 2008/110581 A2 | 9/2008 |
| WO | WO 2013/086516-1 | 6/2013 |
| WO | WO 2013/096845 A2 | 6/2013 |
| WO | WO 2014/147416 A1 | 9/2014 |

OTHER PUBLICATIONS

Pinky Bautista et al., "Digital Staining of Pathological Tissue Specimens with PCA-based Feature Extraction and Linear Mapping of Spectral Transmittance," 13th Color Imaging Conference Final Program and Proceeds, 2005, pp. 63-68.
Kobarg et al., "Numerical experiments with MALDI Imaging data," Adv Comput Math (2014) 40:667-682, Springer Science+Business Media New York 2013.

*Primary Examiner* — Eric S Dejong
(74) *Attorney, Agent, or Firm* — Arent Fox LLP (57) ABSTRACT

A method for computer-assisted analysis of one or more tissue sections of the human or animal body for preparing a digital stain test is provided. During the digital stain test, tissue zones in a tested tissue section with a predetermined clinical picture are detected. Spatially resolved hyperspectral data, particularly mass spectrometry data, is processed for a plurality of measurement positions. Multiple base spectra are determined from the hyperspectral data by obtaining base vectors. The base spectra are correlated with the hyperspectral data such that a plurality of correlation values for the base spectra is obtained for each measurement position. Subsequently, a regression model is calculated using a regression method, the regression model describing a mask of the one or more tissue sections, in which mask diseased tissue zones are marked based on the calculated correlation values. The regression model and the base spectra can then be used to conduct the digital stain test.

14 Claims, 5 Drawing Sheets

METHOD FOR COMPUTER-ASSISTED ANALYSIS OF ONE OR MORE TISSUE SECTIONS OF THE HUMAN OR ANIMAL BODY

CROSS REFERENCE TO RELATED APPLICATION

This application is based upon and claims benefit of priority to German Patent Application No. 102014224916.3, filed Dec. 4, 2014. The disclosure of the prior application is hereby incorporated in its entirety by reference.

The invention relates to a method for computer-assisted analysis of one or more tissue sections of the human or animal body and a method for computer-assisted performing a digital stain test.

In classical pathology, tissue samples are analysed for the purpose of establishing a diagnosis or prognosis of certain medical indications. To this end, tissue sections are processed using biochemical procedures such as HE staining (Hematoxylin-Eosin Staining), immunohistochemical stain tests (also abbreviated to IHC tests) or molecular test procedures. With these procedures, diseased tissue is marked in the tissue section so that the visual inspection and diagnosis are supported. In IHC tests, for example, antibodies are deposited on a tissue section to enable visual identification of biomarkers that are specific to certain clinical pictures.

Mass spectrometric methods for identifying mutated tissue structures are also known from the prior art. Imaging methods originating in mass spectrometry, such as DESI or MALDI, are often used for this. In this context, a full spectrum of mass-to-charge ratios in the range from a few hundred to 10 kDa is captured for each pixel of a tissue section. In this way, a mass spectrum is created that contains one spatial coordinate and one spectral mass-to-charge coordinate in each case. But until now it has not been possible to extract the information contained in this mass spectrometry data in a way that enables mass spectrometric analysis to replace the conventional histological stain test.

The object of the invention is to analyse the hyperspectral data obtained from one or more tissue sections in such a way that said data can be used to conduct digital, that is to say computer-assisted stain tests. It is a further object of the invention to create a method for conducting a digital stain test.

This object is solved with the method according to respective patent claims 1 and 10, and with the apparatus according to respective patent claims 13 and 14. Preferred embodiments of the invention are defined in the dependent claims.

The method according to the invention is used for the computer-assisted analysis of one or more tissue sections of the human or animal body. Each such tissue section was removed from the body by means of biopsy and is processed outside of the body, and once removed the tissue is not returned to the body. Here and in the following, the concept of tissue section is to be interpreted broadly. In particular, a tissue section may also represent a tissue-microarray, in which a number of tissue samples (also called "tissue cores"), preferably taken from different patients, are deposited on a sample carrier. The analysis according to the invention is used to prepare a digital stain test in which tissue zones exhibiting a predetermined clinical picture in a tissue section under test are identified with computer assistance.

In the following, the individual features of the method will be explained as steps a) to e). These steps are intended solely to help the reader understand the interrelationships among the features of the method, they do not necessarily correlate to a chronological sequence in the performance of the steps.

In a step a), spatially resolved (digital) hyperspectral data from one or more predetermined tissue sections to be analysed is read in, wherein the one or more tissue sections have tissue zones with a predetermined clinical picture. The hyperspectral data contains respective spectra for a plurality of spatial (particularly two-dimensional) measurement positions in the one or more predetermined tissue sections, wherein each spectrum represents the composition of the one or more predetermined tissue sections at a measurement position in the form of a vector consisting of intensity values for a plurality of channels, wherein an intensity value is a detected physical parameter for the corresponding channel.

In the case of the analysis of multiple predetermined tissue sections, the measurement positions can be differentiated across all of the tissue sections. In other words, in this case the total number of measurement positions is equal to the sum of all measurement positions contained in the tissue sections, even if measurement positions have the same spatial coordinates in different tissue sections. In order to distinguish between measurement positions from different tissue sections, an index specifying the respective tissue section may be used. The tissue sections are preferably taken from different patients (i.e. different people or animals). In a preferred variant of the invention, between 50 and 100 tissue sections are analysed using the method according to the invention. With an increasing number of tissue sections, the digital stain test carried out on the basis of the results from the analysis method becomes more reliable.

The digital hyperspectral data referred to above may have been captured beforehand and stored in a digital memory, from which they are read out in step a). However, the method according to the invention may also include the step of capturing the hyperspectral data by means of a suitable spectrometer.

The hyperspectral data is preferably mass spectrometry data, particularly "MALDI" mass spectrometry data (MALDI=Matrix-Assisted Laser Desorption/Ionization). In mass spectrometry data, the channels are mass-to-charge ratios, and the physical parameter detected for the corresponding channel represents the number of molecules detected for the corresponding mass-to-charge ratio. Even so, the hyperspectral data may also represent other data, such as data obtained from Raman spectroscopy. In the case of Raman spectroscopy, the channels represent frequencies of light that is reflected or scattered on the tissue sample, and the physical parameter is the intensity of this reflected or scattered light.

In a step b) of the method according to the invention, a (digital) mask of the one or more predetermined tissue sections containing scale values for each of the plurality of measurement positions is read in, wherein zones of the one or more predetermined tissue sections with scale values that differ from (e.g. are higher than) the rest of the zone in the one or more tissue sections are zones with the predetermined clinical picture. The digital mask may have been derived from a conventional histological stain test and particularly from an immunohistochemical stain test of the one or more tissue sections to be analysed. If multiple tissue sections are to be analysed, the mask includes respective submasks for each tissue section. The measurement positions in the submasks are correlated with corresponding measurement positions in the respective tissue sections. As was stated earlier, the measurement positions in this context are differentiated across all of the tissue sections, and thus also across all of the submasks. The digital mask is usually stored in a digital memory beforehead, and the data is read out from this memory in the form of the corresponding scale values. The scale values may originate from a discrete or continuous value range depending on the variant. Optionally, the scale values may also only have the values 0 and 1, wherein the value 0 stands for a tissue zone without the clinical picture, and the value 1 stands for a tissue zone with the clinical picture, or vice versa.

In a step c) of the method according to the invention, multiple base spectra in the space of the hyperspectral data vectors or in a space of derived vectors are determined using a method for calculating base vectors. The derived vectors are calculated from the hyperspectral data for each measurement position. Special variants of the calculation of the derived vectors are described in the following text and in claim 3. The base spectra are the base vectors. The number of base spectra is preferably between 5 and 12. A method for determining base vectors is understood to be a procedure that calculates base vectors in such a way that the vectors of the hyperspectral data or the derived vectors can be represented by combinations (particularly linear combinations) of the base vectors. Preferred variants of methods for determining base vectors are described in the following text.

In a step d) of the method according to the invention, the base spectra are correlated with the vectors of the hyperspectral data or with the derived vectors at each measurement position, with the result that a plurality of correlation values for respective base spectra is obtained for each measurement position. Thus, a correlation value exists for each measurement position and each base spectrum. Methods for correlating vectors are well known. The correlation value is preferably the scalar product between normalised vectors, that is to say between vectors that are multiplied with the reciprocal of their magnitude. In this case, the correlation value lies between −1 and 1. Alternatively, the correlation value may also be the absolute value of the scalar product. In this case, the correlation value lies between 0 and 1 and may be interpreted as a measurement of similarity between the vectors, wherein the vectors become more similar as the correlation value becomes larger.

Finally, in a step e), a regression model (i.e., corresponding parameters of the regression model) is determined with the aid of a regression method. The regression model describes the mask based on the plurality of correlation values for the respective measurement positions. Finally, the regression model with its parameters and the base vectors are stored digitally for use when the digital stain test is carried out later.

The results from the method according to the invention in the form of the base vectors and the regression model can be used to enable computer-assisted stain tests of new tissue sections to be carried out easily, in order to determine whether tissue zones with the predetermined clinical picture are contained in said tissue sections. The concept of the stain test is to be interpreted broadly. In particular, it is not absolutely necessary for the stain test to colour code tissue zones that contain the predetermined clinical picture, instead the coding may be effected generally by means of the scale values described previously.

As described in step c) above, in one variant of the procedure according to the invention, the method for determining base vectors may be applied directly in the space of the hyperspectral data vectors. In this case, results that enable the performance of digital stain tests may be obtained easily without specific information about the biomarkers present in diseased tissue zones. Regardless of this, the base spectra may optionally also be determined in a space of derived vectors, which are determined or calculated from the hyperspectral data for each measurement position. Information about the molecular compositions present in the diseased tissue is preferably used for this purpose, as is the case in the variant of the method according to the invention that will be explained in the following.

In a special variant of the method according to the invention, in which in step c) the base spectra are determined in a space from derived vectors, a derived vector is calculated for each measurement position as explained in the following.

Hyperspectral data (determined either theoretically or experimentally) is prespecified for a plurality of molecular compositions relating to the predetermined clinical picture. In a preferred embodiment, such a molecular composition represents a predetermined peptide and its isotopes. In the case of mass spectrometry data, the hyperspectral data of a peptide is represented by the mass spectrum of the peptide for the various mass-to-charge ratios of its isotopes. Optionally, a molecular composition may also relate to several peptides or other molecules that are represented by hyperspectral data and particularly by a corresponding mass spectrum. The molecular compositions and the associated hyperspectral data were determined beforehand using suitable procedures, wherein such procedures are not a part of the invention and will therefore not be explained in any greater detail.

The hyperspectral data for a molecular composition generally contains a vector in the form of a spectrum of intensity values for a predetermined number of channels from the plurality of channels that is characteristic for the molecular composition. The number of the channels usually represents a fraction of the channels of the hyperspectral data read in in step a) above.

In a following step, the spectra that are characteristic for the molecular composition are correlated with the spectra of the read in hyperspectral data at the respective measurement positions where, as described above, this correlation may be performed on the basis of the scalar product of the normalised vectors. Not all the channels, only the predetermined number of channels is taken into account for the correlation. The result of the correlation is a vector consisting of multiple correlation coefficients and being the derived vector for each measurement position, wherein a correlation coefficient is provided for each molecular composition. Advantageously, between 10 and 200 correlation coefficients exist for each measurement position.

Thus, in the variant of the method according to the invention described above, vectors consisting of the correlation coefficients are obtained from the original hyperspectral data, and these vectors describe the correlation with previously known molecular compositions. In steps c) to e), these derived vectors then undergo further processing instead of the hyperspectral data.

In a particularly preferred variant, the one or more tissue sections to be analysed are each tissue sections with enzymatic digestion. The concept of enzymatic digestion is known from histology. In this process, the tissue section is processed beforehand biochemically. In particular, in the course of enzymatic digestion larger molecules are broken down into peptides by enzymes.

In step c), methods known from the prior art may be used as the method for determining base vectors. In a preferred embodiment, non-negative matrix factorization is used. A Principal Component Analysis (PCA) is also possible. In a particularly preferred variant, the base vectors are determined by non-negative matrix factorization with the side condition of sparse population of the matrices determined using non-negative matrix factorization. In particular, the matrix factorization described in documents [1] and [2] is used. The entire disclosure of these two documents [1] and [2] is herewith included in the content of the present application by reference thereto.

Regression methods known per se can be used in step d) to determine the regression model. For example a linear regression method may be applied in which corresponding weighting factors are specified for the linear combination of the plurality of correlation values for the respective measurement positions. In a further variant of the invention, a Support Vector Machine (SVM) regression, known per se, is applied instead of a linear regression method.

The predetermined clinical picture that is considered in the course of the method described above particularly represents the presence of certain tumour cells. The clinical picture thus relates to a tumour disease. However, the clinical picture may also refer to the presence of insulin islands. In this case, the clinical picture relates to a diabetic disease.

Besides the above method for computer-assisted analysis of one or more tissue sections, the invention relates to a method for computer-assisted performing a digital stain test using base spectra and a regression model, that have been calculated for a predetermined clinical picture and digitally stored using the analysis method described above. In this digital stain test, steps i) to iii) as explained in the following are carried out, where the numbering of the steps does not necessarily imply a chronological sequence of their performance.

In a step i), spatially resolved hyperspectral data from a preset tissue section to be tested is read in, wherein the hyperspectral data contains respective spectra for a plurality of measurement positions in the preset tissue section, wherein a respective spectrum represents the composition of the preset tissue section at a measurement position in the form of a vector consisting of intensity values for channels from a plurality of channels, wherein an intensity value is a detected physical parameter for the corresponding channel. Again, the hyperspectral data is advantageously mass spectrometry data or MALDI mass spectrometry data as described above.

In a step ii), the vectors of the hyperspectral data or derived vectors calculated from the hyperspectral data are correlated at each measurement position with the base spectra, the base spectra having been calculated using the analysis method described above or a preferred variant of said method. In this way, a plurality of correlation values for respective base spectra is obtained for each measurement position. Again, the correlation is preferably calculated from normalised vectors with the aid of a scalar product.

Finally, in a step iii), the regression model that was determined using the analysis method described above or a preferred variant thereof is applied to the correlation values. In the case of a linear regression model, the correlation values for each measurement position are combined with each other linearly on the basis of the weighting factors of the model. With the aid of the regression model, a mask is obtained that contains scale values for each of the plurality of measurement positions, wherein zones of the preset tissue sections that have scale values differing from those of the rest of the tissue section are tissue zones with the predetermined clinical picture.

Thus, digital masks containing information in a manner of a stain test may be generated with the method just described. Preferably, a visualisation is generated on a display device or screen in such manner that an image of the pixels representing the measurement positions is created, wherein each pixel encodes the scale value of the mask determined in step iii) for the measurement position represented by the respective pixel. In this way, a digital representation corresponding to a conventional stain test is created.

In a variant of the digital stain test just described, results of that embodiment of the analysis method according to the invention that is based on derived vectors is used. In this variant of the stain test, derived vectors are correlated in step ii) with the base spectra, and the derived Vectors are calculated as described in the following.

For the predetermined clinical picture, hyperspectral data is prespecified for a plurality of molecular compositions, the molecular compositions being defined in the same way as in the analysis method described above. The hyperspectral data for a molecular composition thus contains a vector in the form of a spectrum of intensity values characteristic of the molecular composition for a predetermined number of channels from the plurality of channels. The spectra that are characteristic of the molecular composition are correlated with the spectra of the hyperspectral data at the respective measurement positions read in in step i), with the result that a vector consisting of multiple correlation coefficients is determined as the derived vector for each measurement position, wherein one correlation coefficient for each molecular composition is present for the respective measurement position.

Besides the method described above, the invention further relates to an apparatus for computer-assisted analysis of one or more tissue sections of the human or animal body for the purpose of preparing a digital stain test, wherein the apparatus is configured to perform the analysis method described above and/or one or more preferred variants of said analysis method. In other words, the apparatus comprises means for carrying out steps a) to e) of the analysis method according to the invention.

The invention also relates to an apparatus for computer-assisted performing a digital stain test using base spectra and a regression model, which were calculated for a predetermined clinical picture and digitally stored using the above analysis method or one or more preferred variants of said method. The apparatus is configured to carry out the digital stain test described above or one or more preferred variants of said stain test. In other words, the apparatus comprises means for carrying out steps i) to iii) of the stain test according to the invention.

The invention additionally relates to a computer program product having a program code stored in a machine-readable carrier for carrying out a method for computer-assisted analysis of one or more tissue sections and/or for computer-assisted performing a digital stain test according to the invention or preferred variants of the invention when the program code is run on a computer.

The invention further relates to computer program having a program code for carrying out a method for computer-assisted analysis of one or more tissue sections and/or for computer-assisted performing a digital stain test according to the invention or preferred variants of the invention when the program code is run on a computer.

In the following, embodiments of the invention will be described in detail with reference to the accompanying figures.

In the following, embodiments of the invention will be explained using hyperspectral data in the form of MALDI mass spectrometry data described above. In the course of this spectrometry technique, the molecules of the tissue section to be analysed are coated with a matrix solution and a laser beam (from a nitrogen laser, for example) is directed at various measurement positions of the corresponding sample carrier. The pulses of the laser beam cause particles of ionised molecules to become detached from the tissue, and the mass-to-charge ratio of these particles is captured in a manner known per se with a mass spectrometer. For this task, for example, a Time of Flight (TOF) or a Fourier Transform Ion Cyclotron Resonance (FTICR) mass spectrometer may be used. However, the methods of the invention described here can also be applied to other mass spectrometry data if necessary, provided the data contains at various measurement positions locally resolved spectra which reflect the number of ions detected by the mass spectrometer as a function of the mass-to-charge ratio. The method of the invention may also be applied generally to hyperspectral data (e.g., Raman spectroscopy) provided the data contains locally resolved intensity vectors with entries for various channels at various measurement positions. An intensity may comprise the portion of reflected or scattered light at a given wavelength, for example, wherein the wavelength represents the channel.

Figure 3:
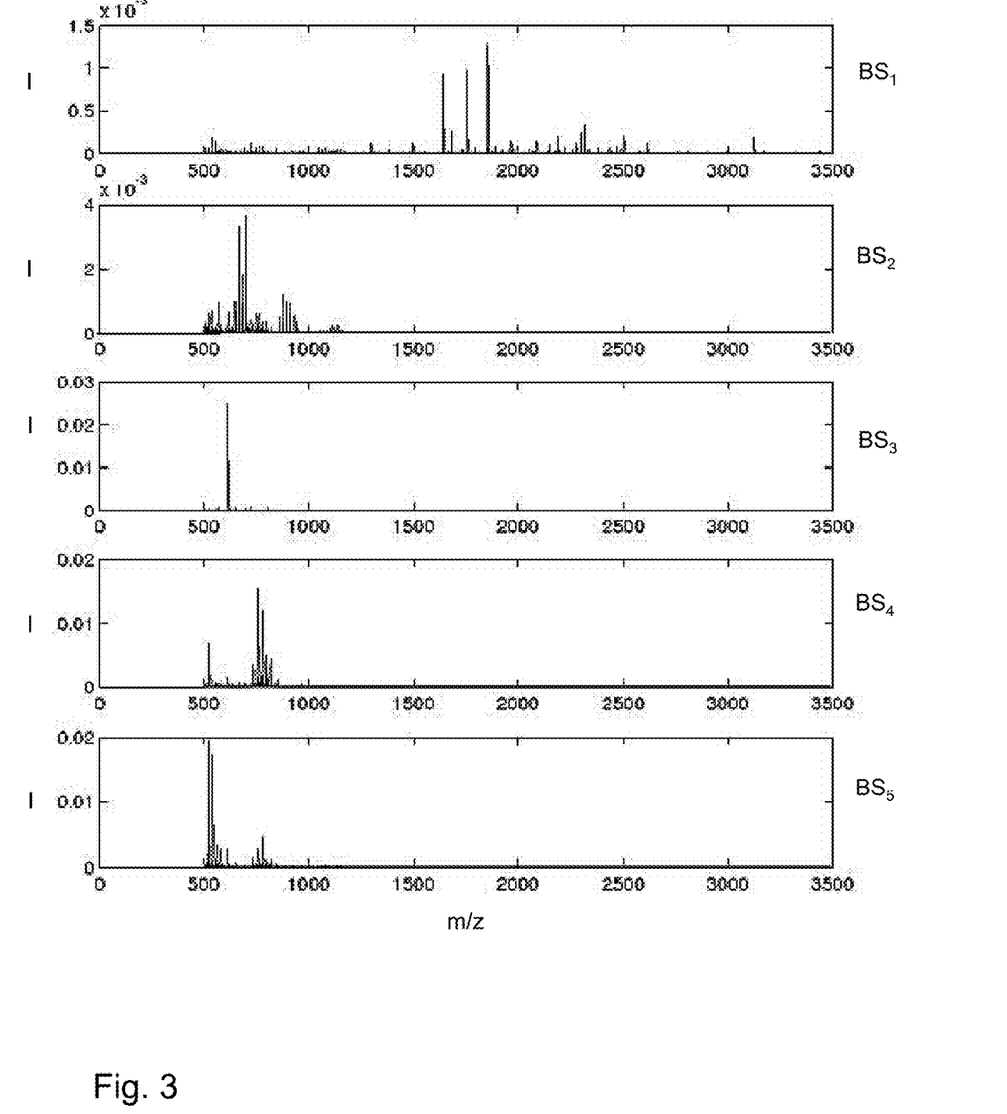
FIG. 3 is a representation showing the base spectra that are calculated in an embodiment of the analysis method according to the invention.
Figure 4:
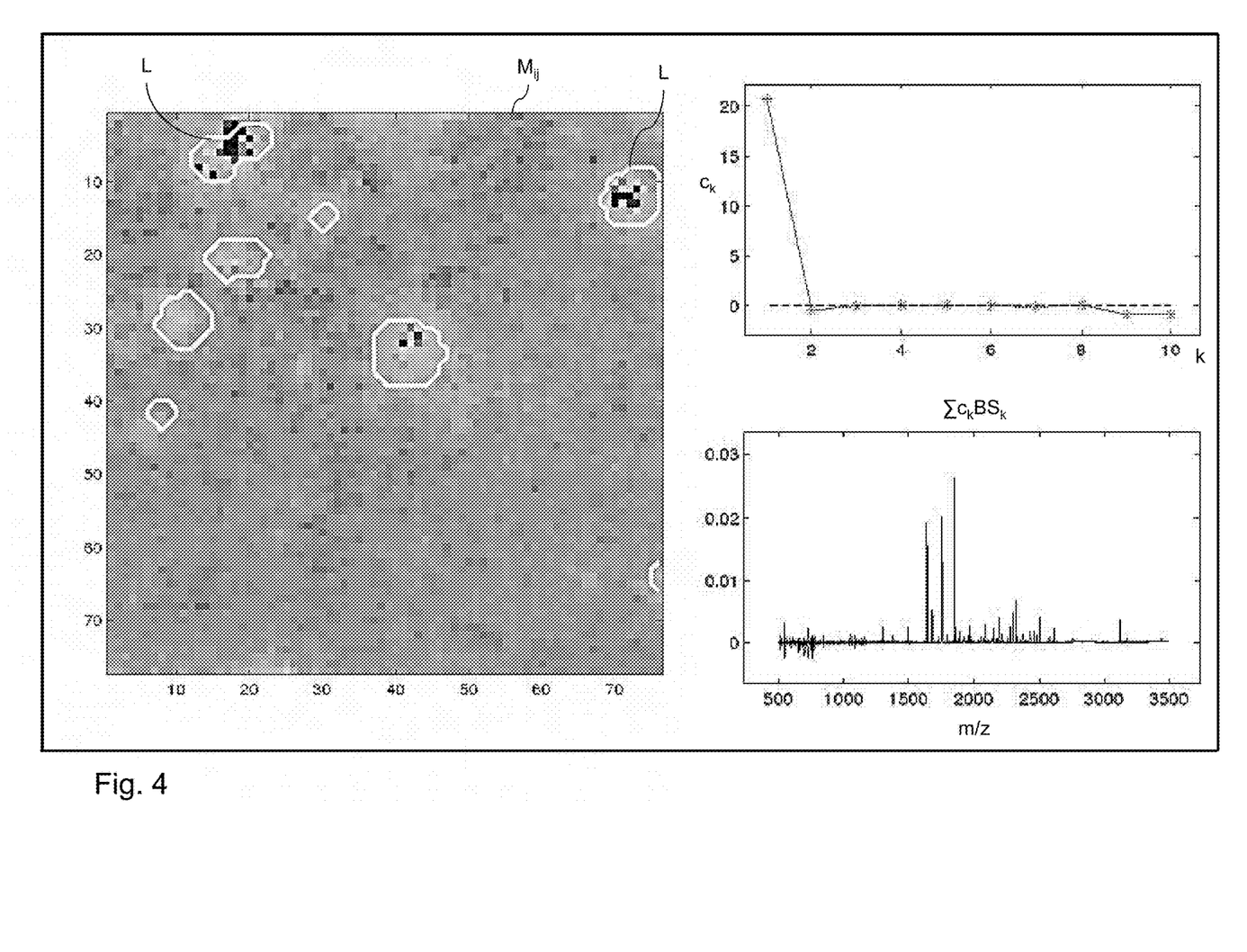
FIG. 4 is a representation showing the calculation of a regression model based on the base spectra of FIG. 3.
Figure 5:
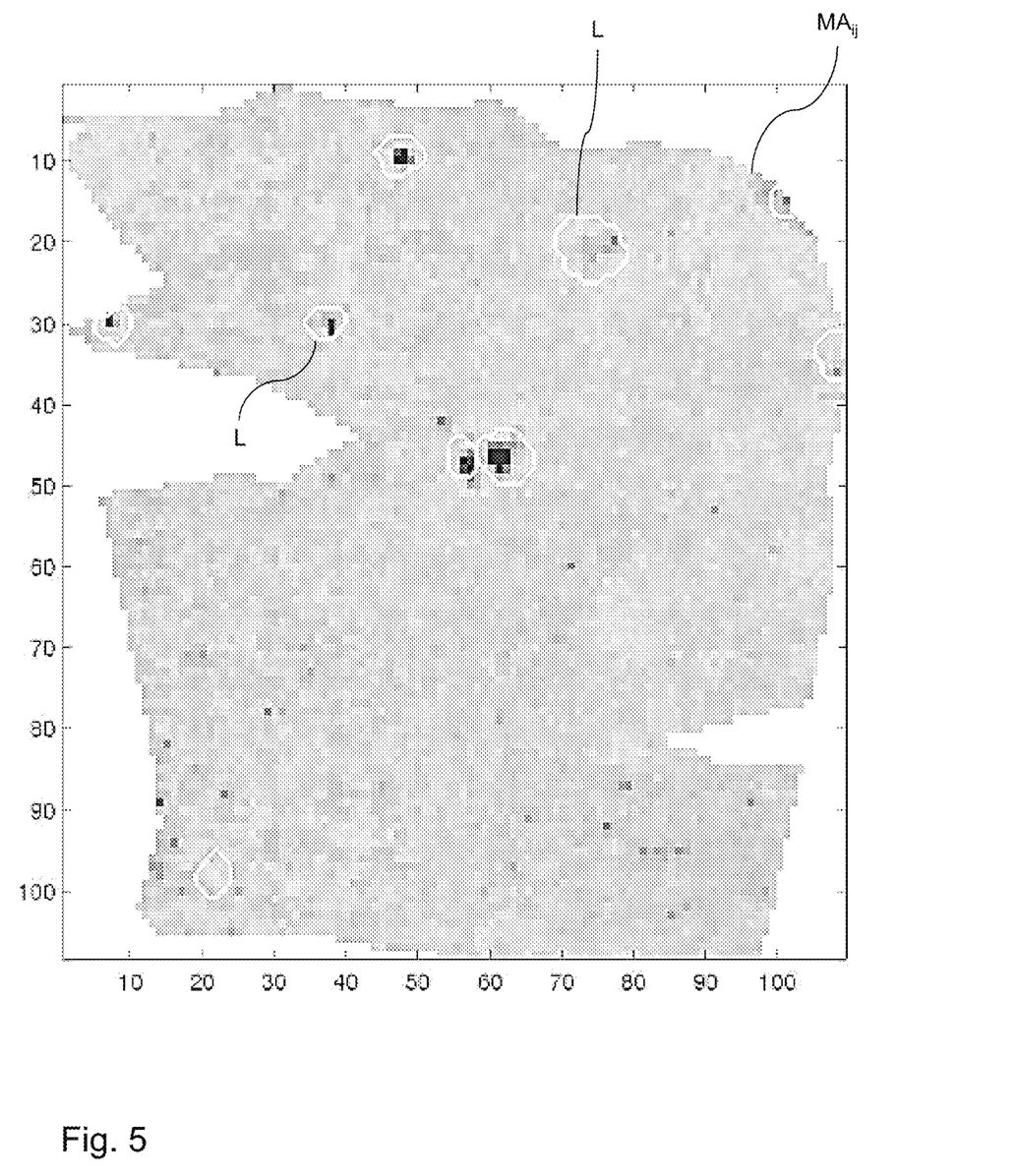
FIG. 5 is a visualization that is generated according to one embodiment of the digital stain test according to the invention.

The next section will first refer to FIG. 1 to explain a method for analysing a tissue section, the results from which are then used in the course of a digital stain test, as will be described afterwards with reference to FIG. 2. FIG. 3 to FIG. 5 show results of the analysis method and the stain test that were obtained using a tissue section from the pancreas of a rat. The corresponding tissue sections include insulin islands in the pancreas, so the tissue sections correspond to the clinical picture for diabetes.

Figure 1:
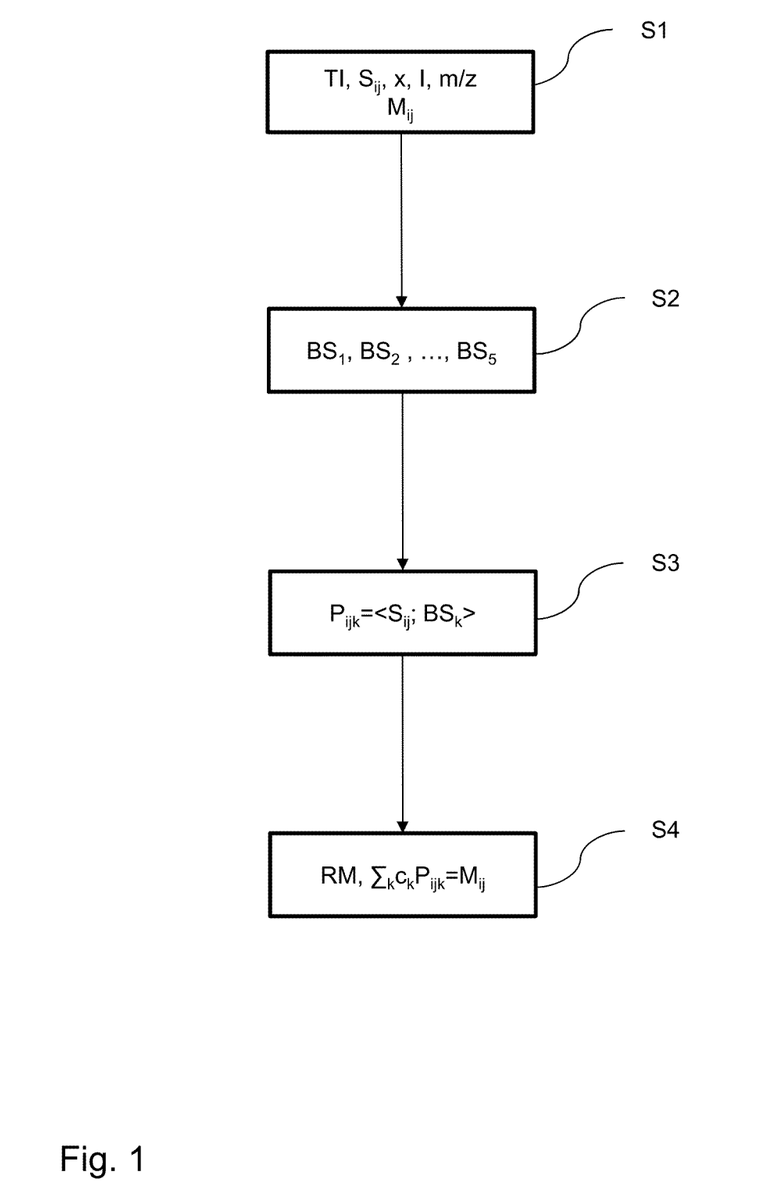
FIG. 1 is a diagram illustrating the steps that are carried out in an embodiment of the analysis method according to the invention.

As part of the analysis method embodiment described here, as shown in FIG. 1, a predetermined tissue section TI that was analysed with MALDI spectrometry described above is considered. Accordingly to this, respective spectra $S_{ij}$ are present at a plurality of two-dimensional measurement positions x of the tissue section, wherein i,j denote the Cartesian coordinates of the respective measurement position. A single spectrum contains intensity values I for a plurality of channels in the form of m/z values (i.e., mass-to-charge ratios), each of which represents the number of the molecules detected for the corresponding m/z value. The method described in the following can be transferred to the analysis of multiple tissue sections, in which case the measurement positions continue beyond the end of the tissue sections. The measurement positions from different tissue sections may be distinguished from each other for example by the use of an index for the respective tissue section.

In a preferred variant, tissue section TI underwent enzymatic digestion before the MALDI spectrometry procedure, so that the molecules of the tissue section were broken down suitably by biochemical processes. For this purpose, enzymes are deposited on the tissue section and split the molecules in the tissue section into peptides. Enzymatic digestion makes it easier to create clinical pictures on the basis of mass spectrometry data in a corresponding tissue section. Besides the mass spectrometry data $S_{ij}$, a (digital) mask $M_{ij}$ of the corresponding tissue section is needed during the analysis of tissue section TI. This mask defines a scale value, between 0 and 1, for example, for the individual measurement positions x of the tissue section. The size of the scale value indicates the size of the fraction of molecules matching the predetermined clinical picture at the respective measurement position. Alternatively, the scale values may also only take the values 0 and 1, in which the value 0 stands for a tissue zone without the clinical picture and the value 1 stands for a tissue zone with the clinical picture. Mask $M_{ij}$ may have been obtained from a conventional immunohistochemical stain test in which biomarkers that are specific for the predetermined clinical picture are highlighted visually by means of tissue staining through the addition of antibodies in the tissue section, and wherein the intensity of the tissue stain indicates the proportion of biomarkers at the corresponding tissue position. The results of the immunohistochemical stain test are then converted into the digital data of mask $M_{ij}$.

As was explained above, the input data for the analysis method described here is the mass spectrometry data $S_{ij}$ and the mask $M_{ij}$, as is shown in step S1 in FIG. 1. This data is read in in digital form, and the step of obtaining the data and particularly the capture of the spectra $S_{ij}$ by mass spectrometric means may also constitute a part of the analysis method.

In a step S2 of the analysis method, spectral signatures in the form of base spectra are then calculated from spectra $S_{ij}$ to differentiate metabolically relevant structures. The five base spectra $BS_1, BS_2, \ldots, BS_5$ are shown in FIG. 1 for exemplary purposes, though more or fewer base spectra can be calculated depending on the variant. The base spectra are calculated using a known method for determining base vectors in the vector space of the spectral data. A respective vector in the vector space represents a single spectrum $S_{ij}$ at a corresponding measurement position, and the entries of the vectors are the intensity values at the m/z values. The base spectra represent the base vectors that are determined using the method. In particular, the base spectra approximate a base in which the spectra $S_{ij}$ are described as a linear combination of the base spectra. In the embodiment described here, a non-negative matrix factorization with the side condition of sparse population of the matrices derived therefrom is used to calculate the base vectors. In this context, the non-negative matrix factorization described in document [1] or document [2] is used. The components in the terminology of document [1] correspond to the base vectors.

In a next step S3, the original spectra $S_{ij}$ are correlated with the base spectra $BS_k$ obtained in step S2 on the basis of a scalar product. This means, corresponding correlation values $P_{ijk}$ for each spectrum $S_{ij}$ and each base vector $BS_k$ are obtained as follows:

$$P_{ijk} = <S_{ij}; BS_k>$$

Correlation value $P_{ijk}$ is normalized to 1 and is located between −1 and 1. For two identical vectors, the correlation value has the value 1. This is achieved by dividing vectors $S_{ij}$ and $BS_k$ by the magnitude thereof before forming the scalar product, and thus normalising them.

Finally, in a step S4, a regression model RM is determined by means of a regression method, which model describes the original mask $M_{ij}$ on the basis of correlation values $P_{ijk}$. In the embodiment described here, a linear regression method is used, in which the mask $M_{ij}$ is approximated by a linear combination of the correlation values, i.e., the following applies:

$$\sum_k c_k P_{ijk} = M_{ij}$$

The weighting factors $c_k$ that are defined using the linear regression method are the parameters of the calculated regression model RM. Any other regression methods instead of a linear regression method may also be used to calculate a regression model that describes the mask as a function of the correlation values. In a particularly preferred embodiment, a Support Vector Machine (SVM) regression method is used.

At the end of the method of FIG. 1, one finally obtains the regression model RM with corresponding parameters $c_k$ and a plurality of base spectra $BS_k$. This information is stored digitally so that it can be used later in a method for carrying out a digital stain test. This method will be explained next with reference to FIG. 2.

Figure 2:
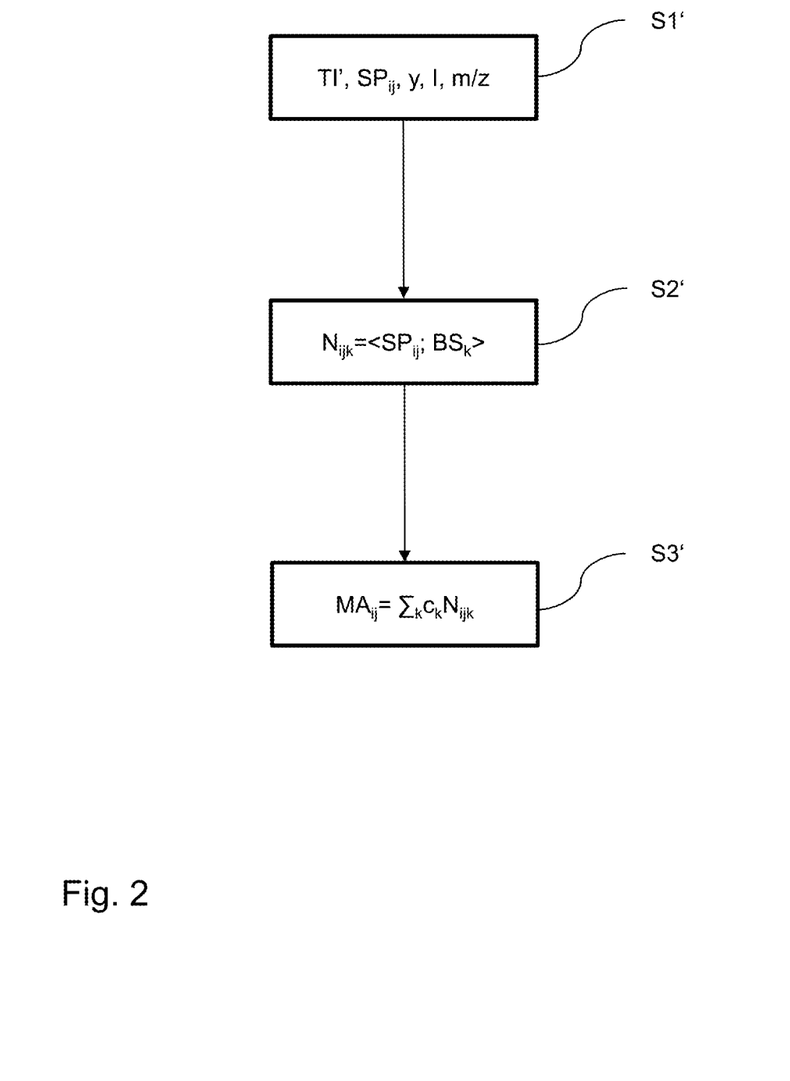
FIG. 2 is a diagram illustrating the steps that are carried out in an embodiment of the digital stain test according to the invention.

The starting point for the method of FIG. 2 is step S1', in which mass spectrometry data $SP_{ij}$ with corresponding intensity values I at the respective m/z values is read in for a plurality of two-dimensional measurement positions y of a tissue section TI' that is to be tested. Optionally, the mass spectrometric measurement to determine the spectra $SP_{ij}$ may itself be included as part of the method. Either way, the data may also have been determined beforehand and read out from a digital memory. For tissue section TI', a mask $MA_{ij}$ shall be generated exclusively on the basis of the mass spectrometry data, and this mask uses appropriate scale values to encode the presence of a predetermined clinical picture at corresponding measurement positions, analogously to the mask $M_{ij}$ of FIG. 1.

In step S2' of the digital stain test, correlation values are now determined in the same way as in step S3 of FIG. 1, but these correlations values are not based on the scalar product between spectra $S_{ij}$ and base vectors $BS_k$, but on the scalar product between spectra $SP_{ij}$ and base vectors $BS_k$. In other words, corresponding correlation values $N_{ijk}$ are obtained as follows:

$$N_{ijk} = <SP_{ij}; BS_k>$$

Like the correlation values $P_{ijk}$ of FIG. 1, the correlation values $N_{ijk}$ are also between −1 and 1. The base vectors $BS_k$ processed in step S2' and the regression model RM processed in the following step S3' are read out from a digital memory and have been calculated with the method of FIG. 1.

In step S3' of FIG. 2, mask $MA_{ij}$ and its scale values are now calculated on the basis of correlation values $N_{ijk}$ and with the aid of regression model RM and the parameters $c_k$ thereof, that is to say it is determined how the correlation values of the spectra of the tissue sample TI' overlap according to the regression model, thus forming mask data $MA_{ij}$. In other words, the mask data is calculated as follows:

$$MA_{ij} = \sum_k c_k N_{ijk}$$

In this way, tissue zones with a predetermined clinical picture are marked correspondingly with computer-assistance by using the results of the analysis method of FIG. 1. Mask $MA_{ij}$ is preferably shown on a display device in the form of a digital image. This image shows tissue section TI' as a plurality of pixels, each of which corresponds to a measurement position of the tissue section. In this way, each pixel encodes the corresponding scale value of mask $MA_{ij}$ on the basis of its grayscale or optionally colour value, so that a colour image is formed, as it is conventionally calculated with an immunohistochemical stain test. According to the invention, however, no biochemical method steps have to be carried out, the colour image value is rather derived entirely from mass spectrometric data with the aid of a computer.

The methods described with reference to FIG. 1 and FIG. 2 represent a "bottom-up" approach, in which the base spectra are obtained using a purely computer-assisted method, without the need for any knowledge of the associated molecular compositions in the tissue sample. In a modified variant ("top-down" approach), it is also possible to determine the base vectors with prior knowledge about the biomarkers and the corresponding peptides into which the biomarkers are broken down by enzymatic digestion. In this context, it was determined or simulated in advance how the known biomarkers decompose into peptides by the action of enzymatic digestion (e.g., trypsin). A mass spectrum providing intensity values in the form of the number of molecules detected for each of the m/z values of the peptide isotopes was also determined for the chemical composition of a respective peptide. Methods for determining the corresponding peptides and their spectra are known per se. Since these methods do not constitute part of the invention, and only the results therefrom are used in the form of peptide spectra, they will not be described in detail.

Based on this modified embodiment, the individual spectra of the peptides are correlated with the spectra $S_{ij}$ from the mass spectrometry data from FIG. 1 in a preprocessing step. Again, correlation is carried out on the basis of a scalar product, wherein in order to generate the scalar product the (normalised) m/z values of the peptide spectra are multiplied with the corresponding (normalised) m/z values of the $S_{ij}$ spectra, and these products are added together. The correlation values obtained thereby, which are called correlation coefficients to distinguish them from the correlation values described above, also lie between 0 and 1. Ultimately, as a result one obtains a number of correlation coefficients corresponding to the number of peptides for each measurement position, which coefficients represent derived vectors in the sense of the patent claims. A method for calculating base vectors, and particularly a non-negative matrix factorization is applied to these derived vectors consisting of correlation coefficients in the same way as in FIG. 1, wherein the base vectors are now calculated in the vector space of the derived vector. These base vectors are then correlated with the derived vectors instead of the original spectra, which again yield correlation values that—as described previously—are determined in such manner that they lie between 0 and 1.

Analogously to step S4 of FIG. 1, a regression model based on these correlation values is then calculated, which describes mask $M_{ij}$.

If the results from the modified embodiment of the analysis method just described are then used for the digital stain test, derived vectors with corresponding correlation coefficients are first calculated by correlating the peptide spectra with the original spectra $SP_{ij}$ before step S2' from FIG. 2 is carried out. Then, analogously to step S2', the correlation values are calculated, though in this case the derived vectors are used. Finally, mask $MA_{ij}$ is determined with the regression model in exactly the same way as in step S3' of FIG. 2.

As was stated above, FIG. 3 to FIG. 5 show the results of an embodiment of the analysis method and of the stain test according to the invention for the tissue section of a rat pancreas, wherein the pancreas contains insulin islands. The tissue section was analysed based on a bottom-up approach. A total of ten base spectra were determined from the original spectra $S_{ij}$, and five of these base spectra $BS_1$ to $BS_5$ are shown in FIG. 3 for exemplary purposes. For the individual base spectra, the corresponding correlation values and the coefficients $c_k$ of a linear regression model were determined. This is shown in FIG. 4.

The ten weighting factors $c_k$ of the regression model for base vectors k=1, . . . , 10 are shown in the diagram at top right in FIG. 4. The diagram at bottom right indicates the superposition of the base spectra corresponding to weighting factors $c_k$, i.e. $\Sigma c_k BS_k$. In addition, an extract from the tissue section with corresponding pixels as image positions x appears in the digital image on the left, and in which the white borders—only some of which are identified with reference letters L in order to preserve clarity—delineate zones in which insulin islands are present in the tissue section. Borders L thus serve to indicate the original mask data, which in the present case only have scale values of 0 or 1, wherein scale value 0 represents a zone without insulin and scale value 1 indicates an insulin island. The individual pixel values in the image shown represent the mask data $M_{ij}$ reconstructed from the calculated regression model, wherein the scale values of the individual pixels are colour coded, though this is not evident from the black-and-white reproduction in FIG. 4. Even so, dark pixel values represent large scale values close to 1. It may thus be seen that the reconstruction is faithful to the original mask data.

Finally, the regression model with the corresponding weighting factors $c_k$ from FIG. 4 was applied to a new tissue section of the rat pancreas. In other words, MALDI mass spectrometry data was determined for the new tissue section, and then mask data $MA_{ij}$ was derived on the basis of steps S2' and S3' of FIG. 2. This mask data is shown for the new tissue section in FIG. 5. Measurement positions y are again individual, colour-coded pixels, though again this is not evident from the black-and-white reproduction in FIG. 5. However, black pixel values represent large scale values. As before, insulin islands in FIG. 5 are indicated by corresponding white borders L (only some of which are designated thereby). Those islands were identified in the real tissue section. As may be seen, the mask data $MA_{ij}$ indicated in FIG. 5 reproduces very effectively the insulin islands that are actually present in the tissue section.

The embodiments of the invention described in the foregoing have a number of advantages. In particular, for the first time it is possible to analyse tissue sections solely on the basis of mass spectrometry methods and so derive pathological tissue zones. The method may thus at least partially replace time-consuming and expensive immunohistochemical tests or other molecular test procedures. To do this, all that is needed is to make a one-time calculation of a regression model and base spectra based on an analysis method, and these can then be used to analyse the mass spectrometry data. In this way, a digital stain test is provided that identifies diseased tissue zones in a tissue section. The tissue section is preferably presented to the pathologist in the form of an image in which diseased zones are reproduced on the basis of colour coding.

LIST OF REFERENCES

[1] DE 10 2013 207 402 A1
[2] J. H. Kobarg et al., "Numerical experiments with MALDI Imaging data", Adv Comput Math (2014) 40, pp 667 to 682, November 2013

The invention claimed is:

1. A computer-implemented method for analysis of one or more tissue sections (TI) of a human or animal body for preparing a digital stain test, wherein in the digital stain test tissue zones that have a predetermined clinical picture are determined in a tested tissue section (TI'), the method comprising:
   a) obtaining spatially resolved hyperspectral data from one or more predetermined tissue sections (TI) that are to be analysed and contain tissue zones having the predetermined clinical picture, wherein the hyperspectral data is mass spectrometry data and contains respective spectra ($S_{ij}$) for a plurality of measurement positions (x) in the one or more predetermined tissue sections (TI), wherein a respective spectrum ($S_{ij}$) represents a composition of the one or more predetermined tissue sections (TI) at a measurement position (x) in the form of a vector consisting of intensity values (I) for a plurality of channels (m/z), wherein an intensity value (I) is a physical parameter detected for a corresponding channel (m/z);
   b) obtaining a mask ($M_{ij}$) of the one or more predetermined tissue sections (TI) containing respective scale values for the plurality of measurement positions (x) wherein zones of the one or more predetermined tissue sections (TI) having scale values that differ from the remaining area of the one or more tissue sections (TI) are tissue zones with the predetermined clinical picture;
   c) determining multiple base spectra ($BS_1, BS_2, \ldots, BS_5$) in a vector space of the hyperspectral data or in a space of derived vectors that are calculated from the hyperspectral data for each measurement position (x) using a method for calculating base vectors;
   d) generating a plurality of correlation values (Pijk) for respective base spectra ($BS_1, BS_2, \ldots, BS_5$) for each measurement position (x) by correlating the base spectra ($BS_1, BS_2, \ldots, BS_5$) with the vectors of the hyperspectral data or with the derived vectors at each measurement position (x); and
   e) generating a regression model (RM) describing the mask ($M_{ij}$) based on the plurality of correlation values ($P_{ijk}$) for the respective measurement positions (x) using a regression method, wherein the regression model (RM) and the base spectra ($BS_1, BS_2, \ldots, BS_5$) are stored digitally.

2. The method according to claim 1, wherein the mass spectrometry data is Matrix-Assisted Laser Desorption/Ionization (MALDI) mass spectrometry data, in which the channels (m/z) represent mass-to-charge ratios and the physical parameter detected for the corresponding channel (m/z) represents the number of molecules detected for the corresponding mass-to-charge ratio.

3. The method according to claim 1, wherein in step c) the base spectra ($BS_1$, $BS_2$, ..., $BS_5$) are determined in the space of the derived vectors, wherein a derived vector is calculated for each measurement position (x) in such manner that for the predetermined clinical picture, hyperspectral data is prespecified for a plurality of molecular compositions, wherein the hyperspectral data for a molecular composition contains a vector in the form of a spectrum characteristic of the molecular composition consisting of intensity values (I) for a predetermined number of channels (m/z) from the plurality of channels (m/z);

the spectra characteristic of the molecular compositions are correlated with the spectra ($S_{ij}$) of the read in hyperspectral data at the respective measurement position (x), with the result that a vector consisting of multiple correlation coefficients is calculated as the derived vector for each measurement position (x).

4. The method according to claim 1, wherein the one or more tissue sections to be analysed are each tissue sections that have undergone enzymatic digestion.

5. The method according to claim 1, wherein the method used in step c) for determining base vectors is a non-negative matrix factorization or a PCA analysis.

6. The method according to claim 5, wherein the non-negative matrix factorization includes the side condition of sparse population of the matrices determined using non-negative matrix factorization.

7. The method according to claim 1, wherein the regression method used in step e) is a linear regression method or an SVM regression method.

8. The method according to claim 1, wherein the mask ($M_{ij}$) in step b) is determined from a histological, particularly an immunohistochemical stain test of the one or more predetermined tissue sections.

9. The method according to claim 1, wherein the predetermined clinical picture represents the presence of predetermined tumour cells or the presence of insulin islands in the one or more predetermined tissue sections (TI).

10. The method according to claim 1, further comprising:
i) obtaining spatially resolved hyperspectral data from a preset tissue section (TI') to be tested, wherein the hyperspectral data contains respective spectra ($S_{ij}$) for a plurality of measurement positions (y) in the preset tissue section (TI'), wherein a respective spectrum ($S_{ij}$) represents the composition of the preset tissue section (TI') at a measurement position (y) in the form or a vector consisting of intensity values (I) for channels (m/z) from a plurality of channels (m/z), wherein an intensity value (I) is a physical parameter detected for the corresponding channel (m/z),
ii) generating a plurality of correlation values (Nijk) for respective base spectra (BS1, BS2, ..., BS5) for each measurement position (y) by correlating the vectors of the hyperspectral data or derived vectors calculated from the hyperspectral data at each measurement position (x) with the base spectra ($BS_1$, $BS_2$, ..., $BS_5$);
iii) obtaining a mask ($MA_{ij}$) that contains respective scale values for the plurality of measurement positions (y), wherein zones of the preset tissue section (TI') with scalar values that differ from the rest of the tissue section (TI') are tissue zones with the predetermined clinical picture, by applying the regression model (RM) to the plurality of correlation values (Nijk).

11. The method according to claim 10, further comprising:
generating a visualization on a display device comprising an image of pixels representing the measurement positions (y), wherein each pixel encodes the associated scale value of the mask ($MA_{ij}$) determined in step iii) for the measurement position (y) represented by the respective pixel (BP).

12. The method according to claim 10, wherein the vectors derived in step ii) are correlated with the base spectra ($BS_1$, $BS_2$, ..., $BS_5$), and the derived vectors are calculated in such manner that for the predetermined clinical picture, hyperspectral data is prespecified for a plurality of molecular compositions, wherein the hyperspectral data for a molecular composition contains a vector in the form of a spectrum of intensity values (I) characteristic of the molecular composition for a predetermined number of channels (m/z) from the plurality of channels (m/z); and the spectra characteristic of the molecular compositions are correlated with the spectra ($S_{ij}$) of the hyperspectral data obtained in step i) at the respective measurement positions (y), with the result that a vector consisting of multiple correlation coefficients is determined as a derived vector for each measurement position (y).

13. An apparatus for computer-assisted analysis of one or more tissue sections (TI) of the human or animal body for preparing a digital stain test, wherein, during the digital stain test, tissue zones in a tested tissue section (TI') that have a predetermined clinical picture are detected with computer assistance, the apparatus comprising:
a) means for obtaining spatially resolved hyperspectral data from one or more predetermined tissue sections (TI) that are to be analysed and contain tissue zones having the predetermined clinical picture, wherein the hyperspectral data is mass spectrometry data and contains respective spectra ($S_{ij}$) for a plurality of measurement positions (x) in the one or more predetermined tissue sections (TI), wherein a respective spectrum ($S_{ij}$) represents a composition of the one or more predetermined tissue sections (TI) at a measurement position (x) in the form of a vector consisting of intensity values (I) for a plurality of channels (m/z), wherein an intensity value (I) is a physical parameter detected for a corresponding channel (m/z);
b) means for obtaining a mask ($M_{ij}$) of the one or more predetermined tissue sections (TI) containing respective scale values for the plurality of measurement positions (x), wherein zones of the one or more predetermined tissue sections (TI) having scale values that differ from the remaining area of the one or more tissue sections (TI) are tissue zones with the predetermined clinical picture;
c) means for determining multiple base spectra ($BS_1$, $BS_2$, ..., $BS_5$) in the vector space of the hyperspectral data or in a space of derived vectors that are calculated from the hyperspectral data for each measurement position (x) using a method for calculating base vectors;
d) means for generating a plurality of correlation values (Pijk) for respective base spectra ($BS_1$, $BS_2$, ..., $BS_5$) for each measurement position (x) by correlating the base spectra ($BS_1$, $BS_2$, ..., $BS_5$) with the vectors of the hyperspectral data or with the derived vectors at each measurement position (x); and
e) means for generating a regression model (RM) describing the mask ($M_{ij}$) based on the plurality of correlation values ($P_{ijk}$) for the respective measurement positions (x) using a regression method, wherein the regression model (RM) and the base spectra ($BS_1, BS_2, \ldots, BS_5$) are stored digitally.

14. A computer program product having a program code stored on a machine-readable medium, wherein the program code when executed on a computer causes the computer to perform the steps of:
   a) obtaining spatially resolved hyperspectral data from one or more predetermined tissue sections (TI) that are to be analysed and contain tissue zones having the predetermined clinical picture, wherein the hyperspectral data is mass spectrometry data and contains respective spectra ($S_{ij}$) for a plurality of measurement positions (x) in the one or more predetermined tissue sections (TI), wherein a respective spectrum ($S_{ij}$) represents a composition of the one or more predetermined tissue sections (TI) at a measurement position (x) in the form of a vector consisting of intensity values (I) for a plurality of channels (m/z), wherein an intensity value (I) is a physical parameter detected for a corresponding channel (m/z);
   b) obtaining a mask ($M_{ij}$) of the one or more predetermined tissue sections (TI) containing respective scale values for the plurality of measurement positions (x), wherein zones of the one or more predetermined tissue sections (TI) having scale values that differ from the remaining area of the one or more tissue sections (TI) are tissue zones with the predetermined clinical picture;
   c) determining multiple base spectra ($BS_1, BS_2, \ldots, BS_5$) in the vector space of the hyperspectral data or in a space of derived vectors that are calculated from the hyperspectral data for each measurement position (x) using a method for calculating base vectors;
   d) generating a plurality of correlation values (Pijk) for respective base spectra ($BS_1, BS_2, \ldots, BS_5$) for each measurement position (x) by correlating the base spectra ($BS_1, BS_2, \ldots, BS_5$) with the vectors of the hyperspectral data or with the derived vectors at each measurement position (x); and
   e) generating a regression model (RM) describing the mask ($M_{ij}$) based on the plurality of correlation values ($P_{ijk}$) for the respective measurement positions (x) with the aid of a regression method, wherein the regression model (RM) and the base spectra ($BS_1, BS_2, \ldots, BS_5$) are stored digitally.

* * * * *